(12) United States Patent
Hahn et al.

(10) Patent No.: US 8,600,506 B2
(45) Date of Patent: Dec. 3, 2013

(54) SYSTEMS AND METHODS FOR COLLECTING PATIENT EVENT INFORMATION

(75) Inventors: Stephen J. Hahn, Shoreview, MN (US); Yanting Dong, Lexington, KY (US); Haresh G. Sachanandani, Culver City, CA (US); Kenneth P. Hoyme, Plymouth, MN (US); James O. Gilkerson, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/568,958

(22) Filed: Aug. 7, 2012

(65) Prior Publication Data

US 2012/0303086 A1   Nov. 29, 2012

Related U.S. Application Data

(62) Division of application No. 12/504,450, filed on Jul. 16, 2009, now Pat. No. 8,260,423.

(60) Provisional application No. 61/081,248, filed on Jul. 16, 2008.

(51) Int. Cl.
*A61N 1/00* (2006.01)
(52) U.S. Cl.
USPC .............................. 607/32; 607/60
(58) Field of Classification Search
USPC ......................... 607/32, 30, 59–60
See application file for complete search history.

(56) References Cited

U.S. PATENT DOCUMENTS

| 5,722,999 | A | 3/1998 | Snell |
| 6,263,245 | B1 * | 7/2001 | Snell ............................. 607/60 |
| 6,535,763 | B1 * | 3/2003 | Hiebert et al. ................. 607/32 |
| 6,665,558 | B2 | 12/2003 | Kalgren et al. |
| 6,978,182 | B2 | 12/2005 | Mazar et al. |
| 7,047,065 | B2 * | 5/2006 | Kalgren et al. ............... 600/510 |
| 7,383,088 | B2 * | 6/2008 | Spinelli et al. ................. 607/30 |
| 7,697,993 | B2 * | 4/2010 | Gilkerson et al. ............. 607/59 |
| 7,801,596 | B2 * | 9/2010 | Fischell et al. ................ 600/523 |

(Continued)

FOREIGN PATENT DOCUMENTS

| EP | 2340084 | 7/2011 |
| JP | 2006525092 | 11/2006 |

(Continued)

OTHER PUBLICATIONS

"Non-Final Office Action," JP Application No. 2008554447, corresponding to U.S. Patent Application No. 2011518915, mailed Sep. 27, 2012, (pp. 1-4).

(Continued)

*Primary Examiner* — Christopher D Koharski
*Assistant Examiner* — Catherine Voorhees
(74) *Attorney, Agent, or Firm* — Pauly, DeVries Smith & Deffner, LLC

(57) ABSTRACT

A method of and system for collecting patient event information is described, where the system includes an implantable medical device (IMD) and an external interface device. The external interface device is remote from the IMD and includes a communication module, a display device adapted to prompt a user of the system to select a reason for a particular transmission session and a user input device adapted to accept input indicating a selected reason.

17 Claims, 9 Drawing Sheets

(56) References Cited

U.S. PATENT DOCUMENTS

| | | | |
|---|---|---|---|
| 7,978,062 B2 * | 7/2011 | LaLonde et al. | 340/539.11 |
| 8,260,423 B2 | 9/2012 | Hahn et al. | |
| 2004/0122484 A1 | 6/2004 | Hatlestad et al. | |
| 2004/0122485 A1 | 6/2004 | Stahmann et al. | |
| 2004/0127958 A1 | 7/2004 | Mazar et al. | |
| 2006/0064136 A1 | 3/2006 | Wang | |
| 2007/0213783 A1 | 9/2007 | Pless | |
| 2008/0162183 A1 | 7/2008 | Sachanandani et al. | |
| 2010/0016920 A1 | 1/2010 | Hahn et al. | |
| 2010/0328320 A1 | 12/2010 | Kerstna et al. | |

FOREIGN PATENT DOCUMENTS

| | | |
|---|---|---|
| JP | 2011528274 | 11/2011 |
| WO | WO-2004098704 | 11/2004 |
| WO | WO-2008008009 | 1/2008 |
| WO | WO-2010009322 | 1/2010 |

OTHER PUBLICATIONS

"Notice of Allowance," mailed May 3, 2012 in co-pending U.S. Appl. No. 12/504,450, "Systems and Methods for Collecting Patient Event Information," (pp. 1-12).

"PCT International Preliminary Report and Written Opinion," from International Application No. PCT/US2009/050861, report issued Jan. 18, 2011, (pp. 1-8).

"PCT International Search Report and Written Opinion," from International Application No. PCT/US2009/050861, corresponding to U.S. Appl. No. 12/504,450, mailed Sep. 30, 2009, (pp. 1-15).

"Response to Communication Pursuant to Rule 161(2) and Rule 162 EPC," Communication dated May 10, 2011, Filed in the European Patent Office on Jun. 10, 2011 for EP Patent Application No. 09790539.2-2305, (pp. 1-12).

"First Office Action", First Office Action from CN Application No. 200980128274.6, mailed Jan. 30, 2013, (40 pgs.) including English translation.

"Second Office Action", from CN Application No. 200980128274.6, mailed Jul. 15, 2013, 35 pages.

* cited by examiner

Please choose the reason for this interrogation session?

- ☐ Hospitalization for heart failure decompensation
- ☐ VT/VF shock received (patient visited clinic)
- ☐ Have leads checked
- ☐ Non-cardiac complications, e.g. stroke, hypertension, etc.
- ☐ Resolve a red or yellow alert
- ☐ Routine follow-up visit
- ☐ Device re-programming before/after procedure
- ☐ Other reason: _____

FIG. 3

SYSTEMS AND METHODS FOR COLLECTING PATIENT EVENT INFORMATION

This application is a divisional of U.S. application Ser. No. 12/504,450, issued on Sep. 4, 2012 as U.S. Pat. No. 8,260,426 which claims the benefit of U.S. Provisional Application No. 61/081,248 filed Jul. 16, 2008, the content of which are herein incorporated by reference in their entirety.

TECHNICAL FIELD

This disclosure relates generally to medical systems and, more particularly, to medical systems that can be used to communicate with implanted medical devices, amongst other things.

BACKGROUND OF THE INVENTION

Implantable medical devices can be used to provide pacing therapy to patients who have cardiac rhythm problems. For example, an implanted cardiac rhythm management (CRM) device can be used to provide pacing therapy to a patient with sinus node dysfunction, where the heart fails to properly initiate depolarization waves, or an atrio-ventricular conduction disturbance, where the conduction of depolarization waves through the heart tissue is impaired.

Implanted medical devices frequently communicate with devices located outside of the body. Such external interface devices are sometimes capable of one-way communication with the implanted device, such as receiving information from the implanted device including sensor information and information about events, such as when the implanted device has provided therapy. This type of external interface device is sometimes referred to as a communicator, which serves to relay information from the device to a computer system where patient information is collected and utilized.

In some cases, an external interface device is capable of two-way communication with the implanted device and can not only receive information from the implanted device, but can also transmit operational parameters to the implanted device, that is, program the device. This type of interface device can be referred to as a programmer and is typically used by a physician or other caregiver in a clinical or hospital setting.

Sometimes, a communicator-type external interface device is provided for use by a patient, often in a patient's home, and can collect information from the implanted device and provide that information to a computer system designed to monitor the patient's status. An exemplary in-home monitoring system is the LATITUDE® patient management system, available from Boston Scientific Corporation, Natick, Mass. Aspects of exemplary in-home monitoring systems are described in U.S. Pat. No. 6,978,182, the content of which is herein incorporated by reference in its entirety.

The existence of in-home monitoring systems such as the LATITUDE® patient management system has provided a large amount of data about patients with implanted medical devices. For example, these systems store information about patient characteristics, device programming, delivery of therapy by the device, and sensor readings. However, additional data regarding patient outcomes and events would be extremely valuable to the scientists and engineers who design the implanted devices.

SUMMARY OF THE INVENTION

Embodiments of the invention are related to medical systems and methods that can be used to communicate with and collect information from implanted medical devices, amongst other things.

In one embodiment of the invention, a method of collecting patient event information from a cardiac rhythm management system (CRM system) is described, where the CRM system includes a cardiac rhythm management device (CRM device) and an external interface device. The method includes the steps of initiating a transmission session wherein the interface device communicates with the CRM device, prompting a user of the CRM system to select a reason for the transmission session, inputting the selected reason for the transmission session to the interface device, and storing the selected reason for the transmission session and timestamp information for the transmission session.

In another embodiment of the invention, a cardiac rhythm management (CRM) system for collecting patient event information includes an implantable CRM device and an external interface device remote from the CRM device. The external interface device includes a communication module adapted to be communicatively coupled to the CRM device and to request information from and receive information from the CRM device during transmission sessions, a display device adapted to prompt a user of the CRM system to select a reason for a particular transmission session, and a user input device adapted to accept input indicating a selected reason. The communication module is configured to transmit the selected reason and timestamp information for the transmission session to the CRM device. The CRM system is adapted to store the selected reason and the timestamp information for the transmission session.

In yet another embodiment of the invention, the CRM system further includes a memory unit, wherein the CRM system is adapted to store the selected reason and timestamp in the CRM device memory unit.

In another embodiment, a system for collecting patient event information includes an implantable medical device (IMD) and an external interface device remote from the IMD. The external interface device includes a communication module adapted to be communicatively coupled to the IMD and to request information from and receive information from the IMD during transmission sessions, a display device adapted to prompt a user of the system to select a reason for a particular transmission session and a user input device adapted to accept input indicating a selected reason. The communication module is configured to transmit the selected reason and timestamp information for the transmission session to the CRM device. The system is adapted to store the selected reason and the timestamp information for the transmission session.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which:

FIG. 3 is one embodiment of a prompt for a display device for collecting event information.

Figure 1:
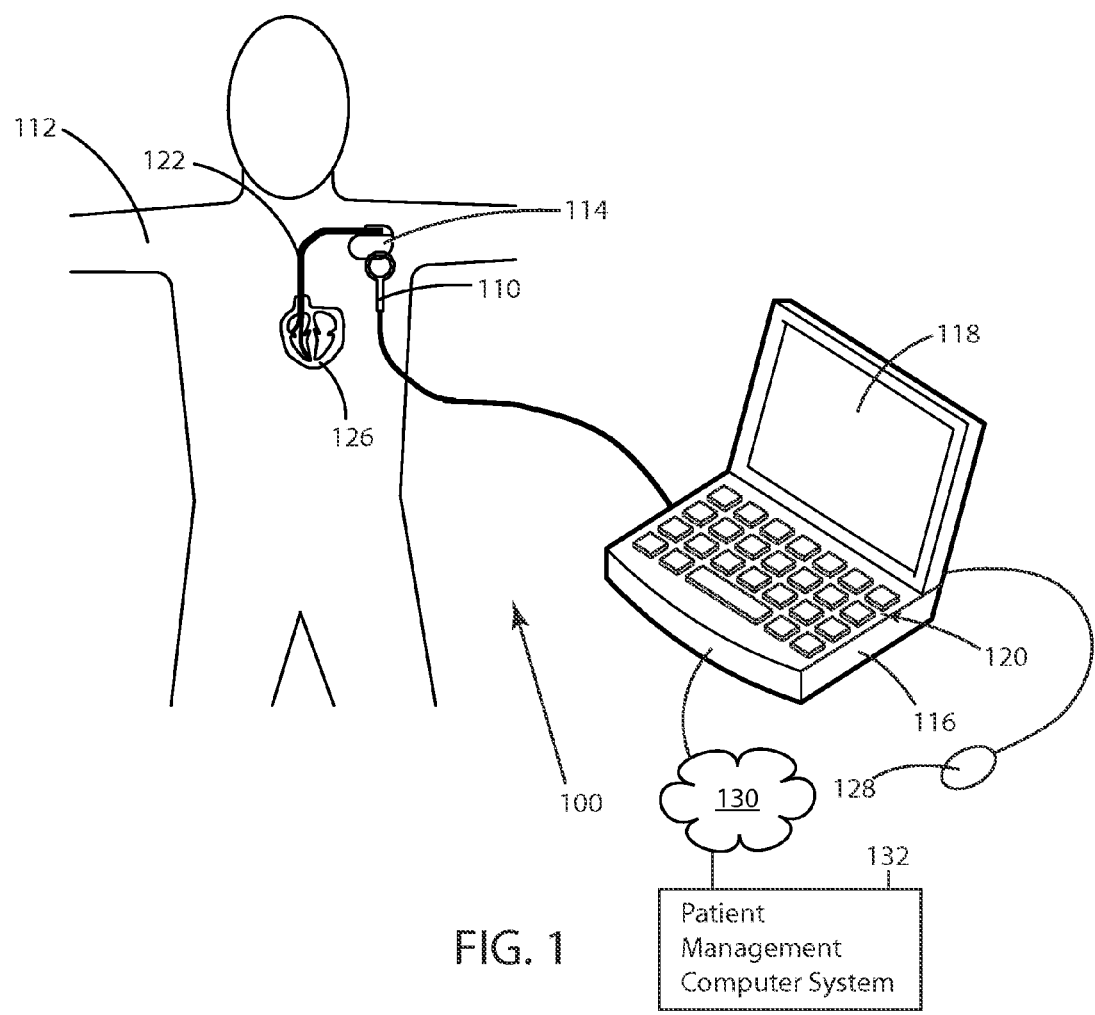
FIG. 1 is a schematic diagram of an exemplary implementation of a cardiac rhythm management (CRM) system, including an implanted CRM device, an external interface device, and a patient management computer system, consistent with at least one embodiment of the invention.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

This disclosure relates generally to medical systems and, more particularly, to medical systems that can be used to communicate with implanted medical devices. In particular, this disclosure relates to the use of external interface devices to gather additional information about the patient's outcome or events. Still more specifically, the disclosure is especially relevant in the context of cardiac rhythm management systems (CRM systems) that include an implantable cardiac rhythm management device (CRM device), an external interface device and a patient management computer system.

An external interface device is frequently paired with an implantable medical device, and this pairing allows communication with the medical device after implantation in a patient. There is a desire for additional patient outcome and event information about patients with implanted medical devices.

For example, a patient with an implanted CRM device and an in-home monitoring system may experience heart failure decompensation symptoms and visit a hospital. The patient may receive treatment, such as a period of hospitalization to stabilize the patient's condition. The patient's device programming may be altered while in the hospital to improve the treatment provided by the CRM device. The patient eventually returns home, where the CRM device is again in communication with the home monitoring system. The device parameter changes will be uploaded to the home monitoring system. However, in the prior art, the occurrence of the decompensation, the hospital visit, or the reason for the parameter changes is not input into or stored in the CRM system. As a result, the occurrence of a hospital visit and the reason for the parameter changes is not present in the patient management computer system. The knowledge of the occurrence of and reason for this type of patient event (hospitalization and device setting changes) would be valuable for scientists and engineers to study. By studying which patients required hospitalization to address cardiac problems and/or reprogramming of their CRM devices, clinicians might find ways to improve device programming and researchers might find ways to improved implanted device designs.

The creation and accurate maintenance of electronic medical records has been discussed for many years and is slowly being implemented in some aspects of health care systems. Electronic medical records could provide this type of patient event information to researchers if electronic medical records were widely created and maintained, if they contained the type of data described above, and if data communication was established between the electronic medical records and monitoring systems for implanted devices. However, a more near-term solution is desirable to collect patient events and outcome information and provide it to researchers and physicians in a matter that links use, parameter settings, or reprogramming of the device to outcomes.

According to embodiments described in this disclosure, an external interface device can be used to gather useful information about why an interrogation or transmission session, such as a device reprogramming session, occurred. For example, after initiation of a transmission session between the external interface device and the implanted device, the interface device may prompt the user to select a reason for the transmission session. The user then inputs the selected reason.

In the context of a CRM system, examples of reasons for the external interface device being used to initiate a transmission session with the CRM device include the patient being in a hospital for heart failure decompensation symptoms and the patient having the device leads checked in a clinic or hospital. Another reason is the patient visiting a clinic or hospital for non-cardiac complications, e.g. stroke, hypertension, etc. Another reason for a transmission session is to that a clinician may change or re-program parameters of the CRM device, which commonly occurs before or after surgery, as well as at other times. All of the foregoing reasons involve a patient's visit to a clinic or hospital. It is also possible to ask a patient to initiate a transmission session remotely from a patient monitoring system. Some reasons for a transmission session may occur either in a clinic or hospital, or at the patient's home or other location. For example, if the patient receives a ventricular tachycardia or ventricular fibrillation (VT/VF) shock, the patient may visit a healthcare provider. Alternatively, the patient may communicate with a healthcare provider by phone or e-mail who may instruct the patient to initiate a remote transmission session. The remote transmission session causes the most recent device information to be uploaded to the patient management computer system so that the provider can review it without requiring the patient to travel to a clinic.

In another situation, the patient management computer system or the CRM device issues an alert. Generally, the alerts are color-coded to indicate urgency. A red or yellow alert indicates that the patient should be evaluated by a healthcare provider. The patient may do so by visiting a clinic or hospital. Alternatively, the clinic or doctor can ask the patient to initiate a remote interrogation session in order to investigate and hopefully resolve a red or yellow alert. Other reasons are possible, and the user of the external interface device can be provided with an entry field to describe and annotate any other reason.

The reason selected by the user as the reason for the transmission session may be stored in the CRM device. When the CRM device next communicates with the patient management computer system, the reason can be uploaded to the patient management computer system. Once the data is stored in the patient management computer system, it will be accessible to researchers who study data in those systems. In the future, this type of event or outcome information may lead to early identification of patients who experience a hospitalization.

If a patient initiates a remote interrogation session and either enters a reason or does not choose a reason, the reason for the interrogation session may be modified or verified by the clinic or hospital when they review the information from the interrogation session.

There are many different types of and possible configurations for the external interface device. Generally, external interface devices are capable of wirelessly communicating with an implanted medical device. The external interface device can at least establish a transmission or interrogation session with the implanted medical device and receive information. The information from the implanted medical device can include sensor readings, parameter settings, and data about the delivery of therapy. The external interface device may include a communication module adapted to be communicatively coupled to the implanted medical device, a display device, and a user input device.

The external interface device may be called a programmer and may be designed for use in a clinic or hospital setting, in which case the programmer has the ability to change the device settings of the implanted medical device. The external interface device may be called a communicator and be designed primarily for use by the patient, either in the patient's home or at another location of the patient, or the communicator may be sized to be carried by the patient, similar to a cell phone. As the term is used in this application, a communicator is not capable of programming the CRM device.

In some embodiments, the external interface device communicates with a patient management computer system to provide patient-related data. Examples of information that may be provided to the patient management computer system include device settings, sensor readings, and a record of therapy provided to the patient by the implanted devices.

Further detailed embodiments will now be described with respect to the attached FIGS.

One embodiment of a CRM system will now be described with reference to FIG. 1. FIG. 1 is a schematic of an exemplary CRM system 100, consistent with at least one embodiment of the invention. The system 100 can include an implantable medical device 114 disposed within a patient 112. The implantable medical device 114 can include pacing functionality. The implantable medical device 114 can be of various types such as, for example, a pacemaker, a cardioverter-defibrillator, a cardiac resynchronization device, or the like. In some embodiments, the implantable medical device 114 can include one or more leads 122 disposed in or near the patient's heart 126.

The implantable medical device 114 can be in communication with an external interface device 116. In some embodiments, communication between the implantable medical device 114 and the external interface device 116 can be via inductive communication through a wand 110 held on the outside of the patient 112 near the implantable medical device 114. However, in other embodiments, communication can be carried out via radiofrequency transmission, acoustically, or the like.

The implantable medical device 114 can include one or more implantable sensors in order to gather data regarding the patient 112. For example, the implantable medical device 114 can include an activity level sensor, a respiration sensor, a blood pressure sensor, or other sensors.

The implantable medical device 114 can be configured to store data over a period of time and periodically communicate with the external interface device 116 in order to transmit some or all of the stored data.

The external interface system 116 can be, for example, a programmer, a programmer/recorder/monitor device, a computer, an advanced patient management system, a personal digital assistant (PDA), or the like. As used herein, the term programmer refers to a device that programs implanted devices, records data from implanted devices, and allows monitoring of the implanted device. Exemplary programmer/recorder/monitor devices include the Model 3120 Programmer, available from Boston Scientific Corporation, Natick, Mass. The external interface device 116 can include a user input device, such as a keyboard 120 and/or a mouse 128. The external interface device 116 can include a video output channel and video output device, such as a video display 118 for displaying video output. The displayed video output can include a user interface screen. In addition, the video display 118 can also be equipped with a touch screen, making it into a user input device as well.

The external interface device 116 can display real-time data and/or stored data graphically, such as in charts or graphs, and textually through the user interface screen. In addition, the external interface device 116 can present a textual question to a user along with several response options. The external interface device 116 can also input and store a user's response to the question and can store a user's text response in some embodiments.

In one embodiment, the external interface device 116 is in communication with a patient management computer system 132. The communication link between the external interface device 116 and the patient management computer system 132 may be via phone lines, the Internet 130, or any other data connection. In another embodiment, the external interface device 116 is not in direct communication with the patient management system.

In one embodiment, the external interface device 116 is capable of changing the operational parameters of the CRM device 114 and is therefore referred to as a programmer. Typically, programmers are used to interface with CRM devices in a clinic or hospital setting. In this context, the user of the external interface device is a physician or trained technician.

Figure 2:
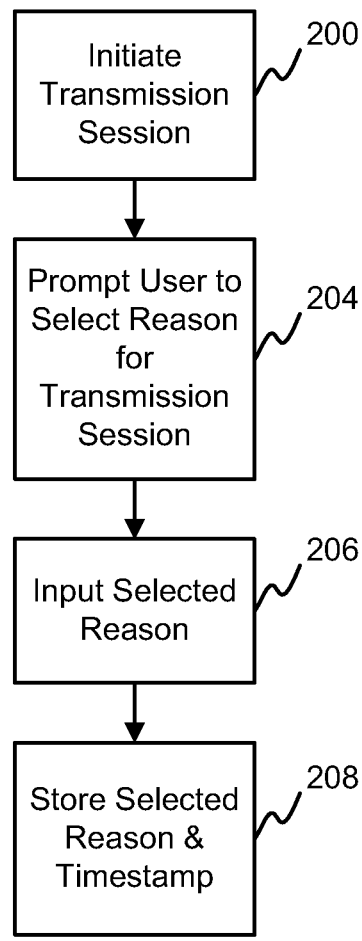
FIG. 2 is a flowchart showing one embodiment of a method of collecting event information.
Figure 4:
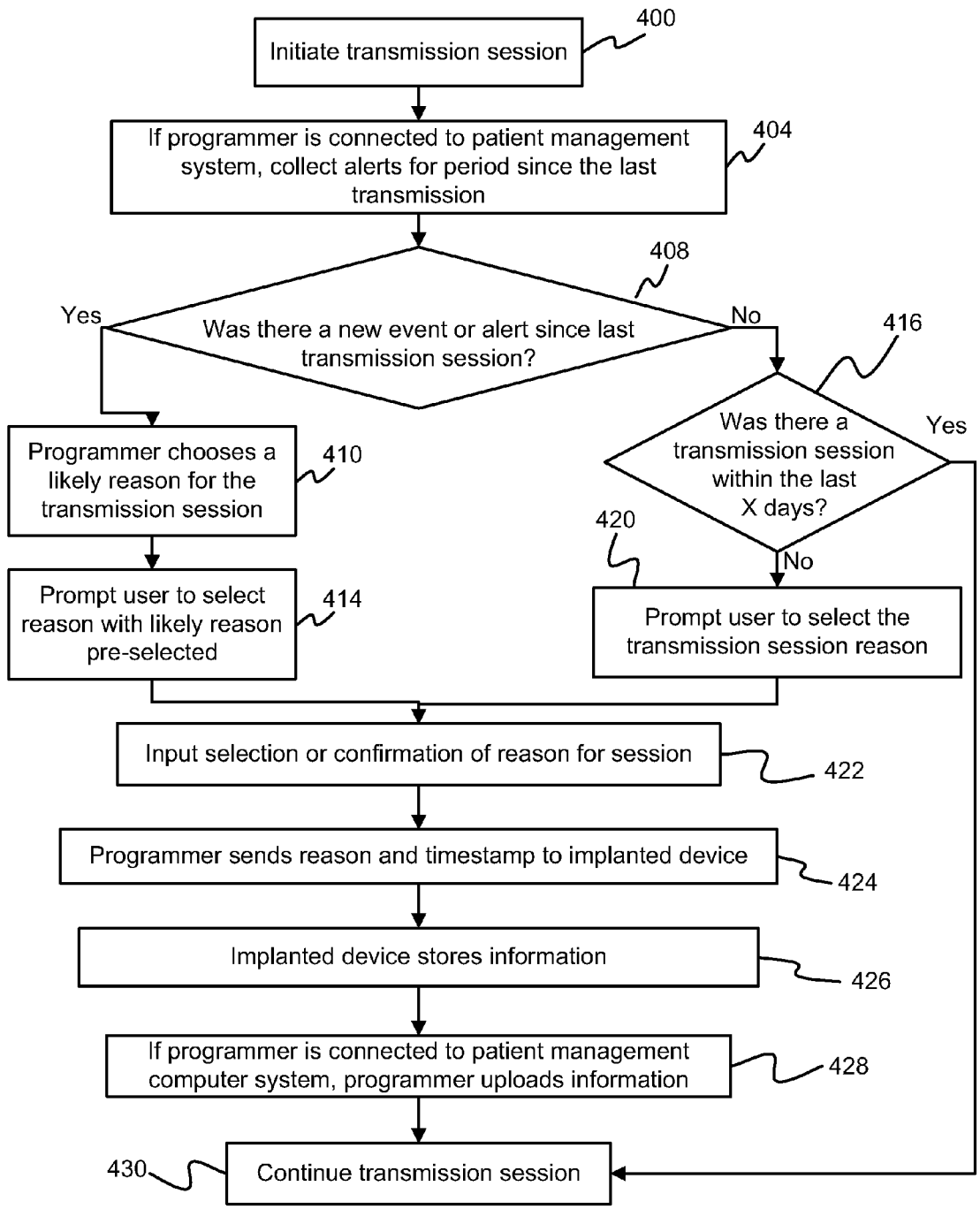
FIG. 4 is another flowchart showing a different embodiment of a method of collecting event information.

One method of collecting patient event and outcome information will now be described with reference to FIG. 2. A transmission session is initiated at step 200 between an implantable or implanted medical device and an external interface device. Then, the user is prompted to select a reason for the session at step 204. This prompt can appear on the display of the external interface device 116. Examples of such prompts are shown in FIGS. 3 and 4 and will be further described. The user inputs the selected reason for the interrogation session at step 206. The CRM system stores the selected reason and a timestamp of the interrogation session at step 208.

There are many different ways that the CRM system can store the selected reason and a timestamp of the transmission session. In one embodiment, the external user interface device receives the user's response and transmits that information to the implanted CRM device. The selected reason and timestamp for the transmission session are stored in the memory unit of the CRM device. The next time that the CRM device communicates with the patient management computer system, the selected reason and timestamp for the transmission session are sent to the patient management computer system.

It is also possible that the external interface device is capable of communication with the patient management system and that the external interface device can store the selected reason and time until it communicates with the patient management system.

In many scenarios, the step 204 of prompting the user to select a reason for the interrogation session occurs immediately after the interrogation session is initiated. In some scenarios, step 204 of prompting the user to select a reason for the interrogation session occurs later in time, after the interrogation session has ended and when the downloaded information from the interrogation session is being examined. Some of the different possible prompts and scenarios will now be described.

FIG. 3 illustrates an example of a prompt 300 that may be shown to a user of the CRM system. In particular, the prompt 300 of FIG. 3 is adapted to be shown on a video display device of a programmer in use in a hospital or clinic. The user is presented with a list of choices 304 of reasons for the transmission session. The list of choices 304 in this embodiment includes hospitalization for heart failure decompensation, that a VT/VF shock has been received by the patient, having leads checked, having non-cardiac complications such as a stroke or hypertension, and resolving a red or yellow alert.

Other reasons offered are a routine follow-up visit and a device reprogramming before or after a procedure, such as a surgery or imaging procedure. For example, it is often desirable to turn off tachycardia detection and therapy if electrocautery will be used in a surgery and if certain imaging procedures are performed, such as an MRI or a CT scan. Other programming changes may be desirable before a particular procedure as well.

In addition to these reasons, the user is offered the choice of "other reason" and provided with a field 308 for describing the other reason. For example, a transmission session can occur in response to a patient complaint or request, such as a complaint about shortness of breath, fatigue, non-cardiac stimulations, or beeping. These reasons can be described in the field 308. Alternatively, additional reasons may be provided within the prompt 300. Each of the reasons in the list of reasons 304 has a checkbox 310 provided so that the user can select one of the reasons.

FIG. 4 illustrates another embodiment of the steps of a CRM system. First, a transmission session is initiated at step 400. If the external interface device is connected to a patient management system, the external interface device collects information about any alerts issued by the patient management session during the period since the last transmission session at step 404. Next, the system checks to see if a new event or alert has been issued by either the patient management system or the CRM device since the last transmission session at step 408. An example of an event that would be recorded by the CRM device includes the administration of a VT/VF shock. If the answer to the query at step 408 is yes, then the programmer chooses a likely or anticipated reason for the transmission session at step 410 that aligns with the recent event or alert information. For example, if there was a VT/VF shock administered since the last transmission session, then the programmer chooses an anticipated reason for the transmission session as administration of a VT/VF shock. If there was a red or yellow alert since the last transmission session, the system chooses an anticipated reason of resolving the red or yellow alert. In another example, the various sensor information collected by the CRM device may have been analyzed either by the CRM device itself or by the patient management system to detect a heart failure decompensation event.

Next, the user is provided with the anticipated reason along with a list of other possible reasons at step 414. The anticipated reason can be indicated by the presence of a check in a checkbox 310. The user can quickly accept the anticipated reason or can uncheck the anticipated reason if it is incorrect.

To further assure the accuracy of the collected data by eliminating redundant prompts, a filter can be applied to the process of prompting the user for a reason for the transmission session. Redundant prompts may arise when multiple transmission sessions follow a particular event. If the answer to the query at step 408 was no, then the system may optionally check to see if there was a transmission session within a previous time period, such as within a certain number of days, at step 416. If no transmission session and accompanying prompt occurred within the certain number of days, then the user is prompted to select the reason for the transmission session at step 420. The number of days used in the filter may be 1, 2, 3, 4, or other numbers.

In one embodiment, the number of days used in the filter varies depending on the reason entered for the previous transmission session. For example, in box 416, X may be one day if the reason for the previous transmission session was a lead check or for VT/VF shock received. In another example, X may be seven days if the reason for the previous transmission session was a hospitalization.

The input of the selection or confirmation of the reason for the session is received at step 422. The external interface device sends the reason and the timestamp to the CRM device for storage of that information at step 424. The implanted device stores the event information at step 426. If the external interface device is connected or later connected to the patient management computer system, then it uploads the reason and timestamp information to the patient management computer system at step 428. The transmission session continues at step 430.

Steps 408-414 of pre-selecting an anticipated reason for the transmission session are optional steps. Likewise, step 416 of applying a filter is an optional step.

Figure 5:
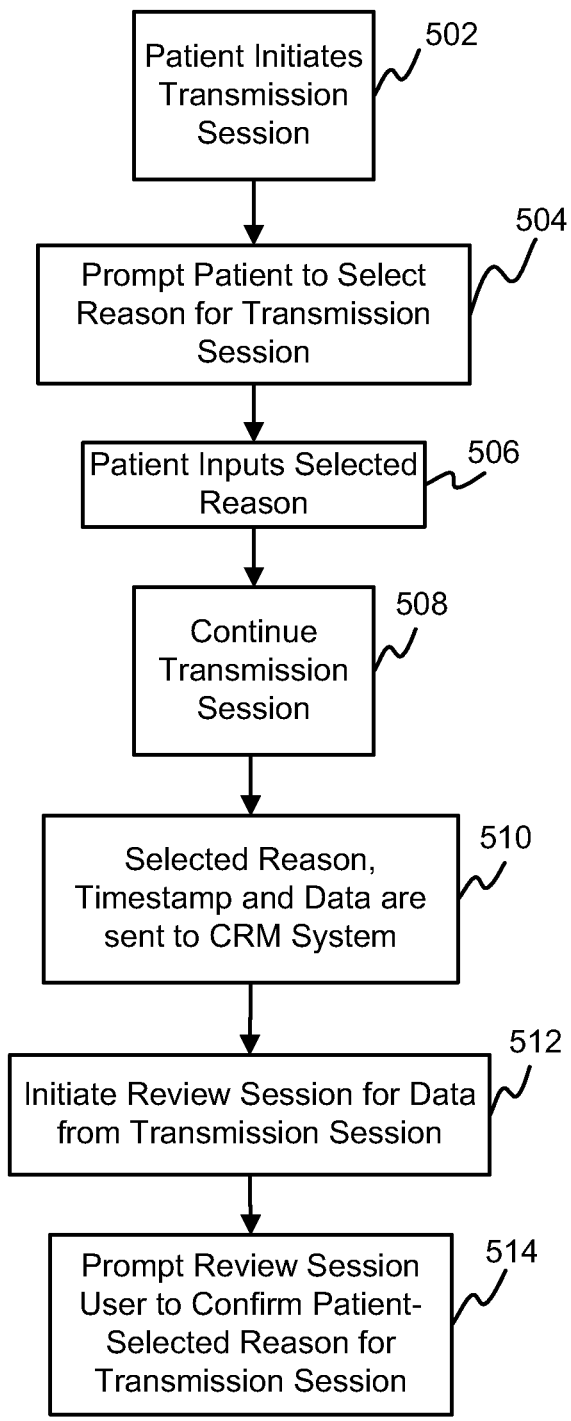
FIG. 5 is another flowchart showing yet another embodiment of a method of collecting event information.

The steps of FIG. 4 can apply to transmission sessions initiated either by a programmer or a patient-operated communicator. Now the steps of FIG. 5 will be described, which shows steps that are especially suited for the situation where a patient initiates a transmission session when they are remote from a hospital or clinic.

Many CRM devices are equipped with an option for the patient to initiate a transmission session. This may occur in a number of different situations as previously discussed herein. Now referring to FIG. 5, a patient initiates a transmission session with an implanted device at step 502 using an external interface device, such as a communicator. A display device of the communicator prompts the user to select a reason for the session at step 504, which may include a list of appropriate reasons from which the patient can select.

Figure 6:
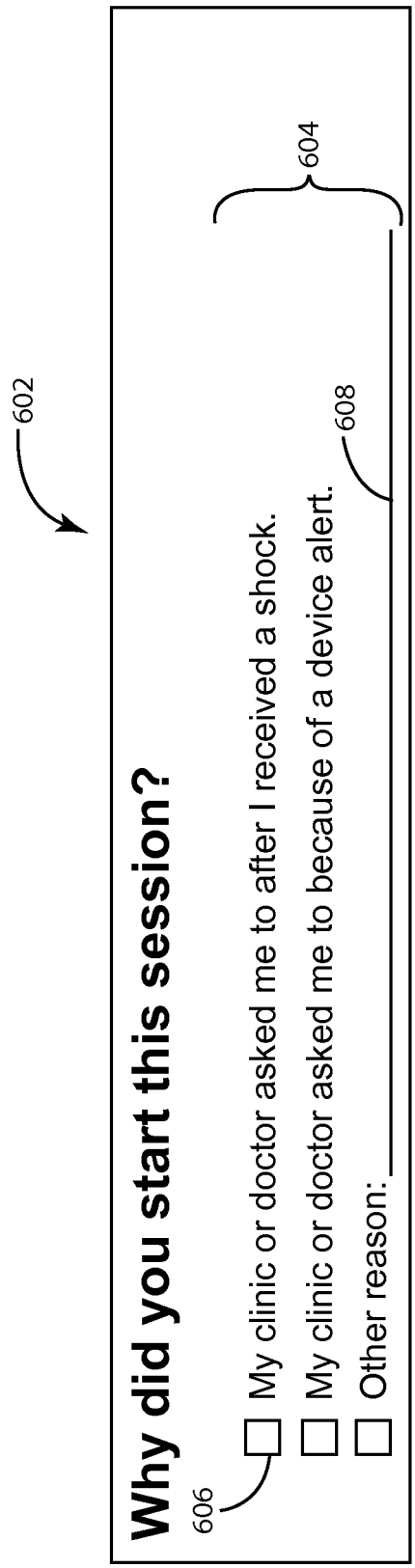
FIG. 6 is another embodiment of a prompt for a display device for collecting event information.

FIG. 6 is an example of a prompt 602 that may be presented to the patient. The patient may be asked, "Why did you start this session?"

The patient may also be presented with a list of reasons 604 from which to choose, where each reason can be selected using one of the checkboxes 606. Examples of reasons that would be relevant to a patient who is conducting a remote monitoring session include that the patient was asked to initiate a session after receiving a shock, that the patient was asked to initiate a session because of an alert, and other reasons that the patient can describe in a field 608.

Again referring to FIG. 5, after the patient is prompted to select a reason at step 504, the patient inputs a selected reason at step 506, such as by checking a check-box. It is also possible that an anticipated reason has been selected by the system in response to recent events, as described above with respect to FIG. 4.

Then the transmission session continues and concludes at step 508, resulting in the selected reason, timestamp, and interrogated data being sent to the patient management computer system at step 510. Later, personnel at the clinic review the data downloaded during the remote transmission session at step 512. At the beginning of the review session, the system may prompt the user to confirm the patient-selected reason for the transmission session, or enter a different reason, at step 514.

Figure 7:
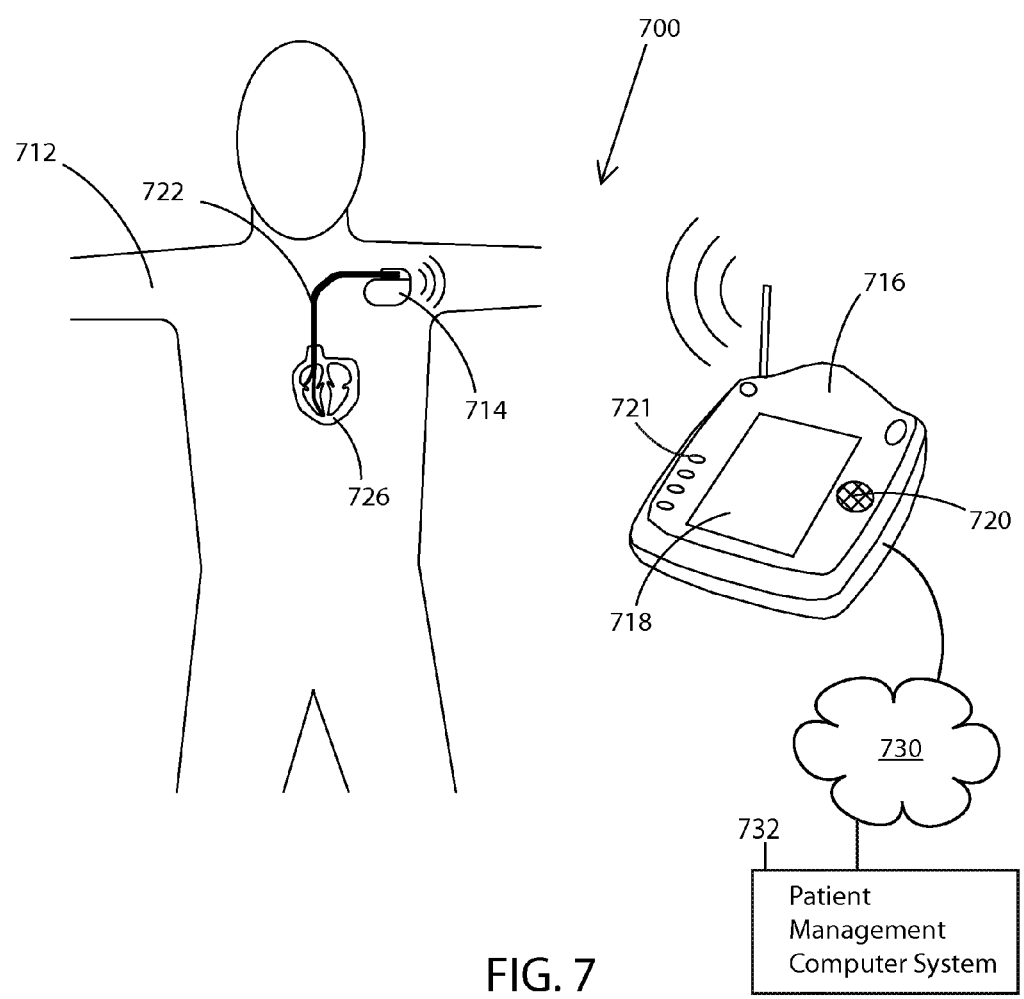
FIG. 7 is a schematic diagram of an exemplary implementation of another CRM system, including an implanted device, a different external interface device, and a patient management system, consistent with at least one embodiment of the invention.

It will be appreciated that the external interface device can be used to display the user interface screen of various embodiments herein can take on many different forms. FIG. 7 is a schematic of one embodiment of a system 700 that is particularly suited to use in a patient's home. An implantable device 714, implanted within a patient 712, is in communication with an external interface device 716 that can have a visual output in the form of a display screen 718 and an audio output in the form of a speaker 720. In some embodiments, the implantable medical device 714 can include one or more leads 722 disposed in or near the patient's heart 726. Buttons 721 provide a means for patient input. In addition, the display screen 718 may be a touch screen which provides additional avenues for patient input. Communication with the implantable device 714 can be through radio frequency, inductive transmission, acoustically, or any other means available.

The external interface device 716 can be a component of a patient monitoring system for use by a patient in his home or residence. An exemplary in-home monitoring system is the LATITUDE® patient management system, available from Boston Scientific Corporation, Natick, Mass. Aspects of exemplary in-home monitoring systems are described in U.S. Pat. No. 6,978,182, the content of which is herein incorporated by reference in its entirety. In such a situation, the external interface device 716 can be in communication with an additional processing device such as a workstation or server located remotely from the external interface device 716 to enable access to the information by doctors or technicians. For example, the external interface device 716 can be in communication with a patient management computer system 732 through the Internet 730 or another type of data connection. In some embodiments, the external interface device can be a mobile device (not shown), such as a hand-held device or a device worn on a belt.

In some embodiments, the invention includes a device including a graphical display and a machine-readable medium comprising instructions. The instructions can perform various operations when implemented by one or more processors. By way of example, the operations can include those in accordance with methods as described herein. The machine-readable medium can include random access memory (RAM), read-only memory (ROM), magnetic data storage media, optical data storage media, flash memory, and the like.

Figure 8:
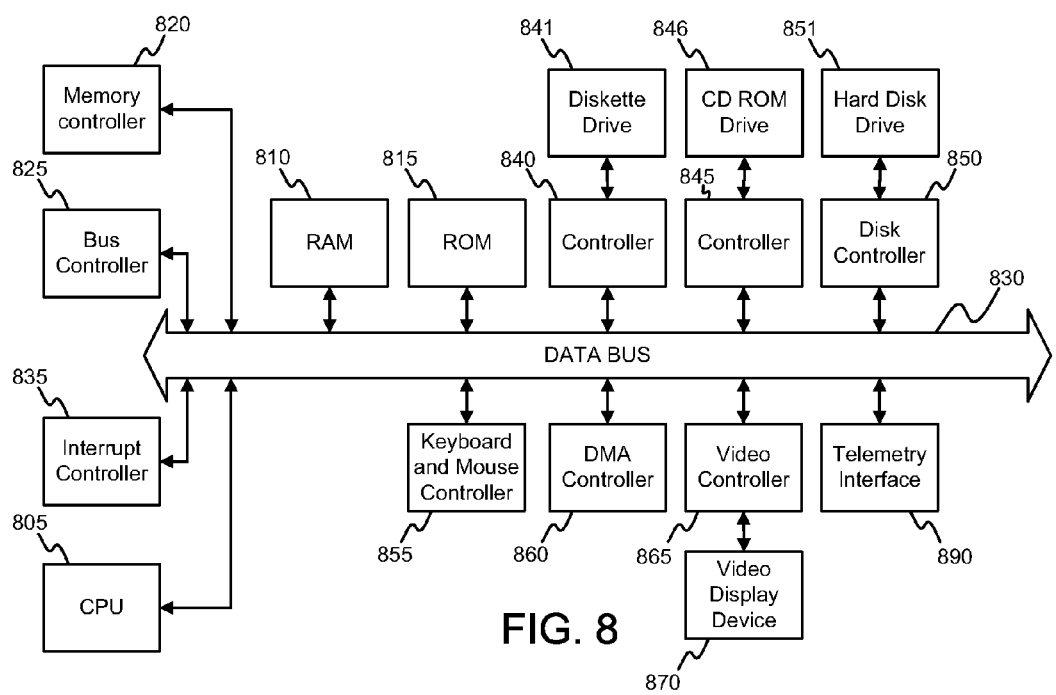
FIG. 8 is a schematic diagram of an implementation of the components of an external interface device, in accordance with various embodiments.

External interface devices to display information, such as programmer/recorder/monitors, can include components common to many computing devices. Referring now to FIG. 8, a diagram of various components is shown in accordance with some embodiments of the invention. However, it is not required that an external interface device have all of the components illustrated in FIG. 8.

In one embodiment, the external interface device includes a central processing unit (CPU) 805 or processor, which may include a conventional microprocessor, random access memory (RAM) 810 for temporary storage of information, and read only memory (ROM) 815 for permanent storage of information. A memory controller 820 is provided for controlling system RAM 810. A bus controller 825 is provided for controlling data bus 830, and an interrupt controller 835 is used for receiving and processing various interrupt signals from the other system components.

Mass storage can be provided by diskette drive 841, which is connected to bus 830 by controller 840, CD-ROM drive 846, which is connected to bus 830 by controller 845, and hard disk drive 851, which is connected to bus 830 by controller 850. User input to the programmer system may be provided by a number of devices. For example, a keyboard and mouse can be connected to bus 830 by keyboard and mouse controller 855. DMA controller 860 is provided for performing direct memory access to system RAM 810. A visual display is generated by a video controller 865 or video output, which controls video display 870. The external system can also include a telemetry interface 890 or telemetry circuit, which allows the external system to interface and exchange data with an implantable medical device. It will be appreciated that some embodiments may lack various elements illustrated in FIG. 8.

Figure 9:
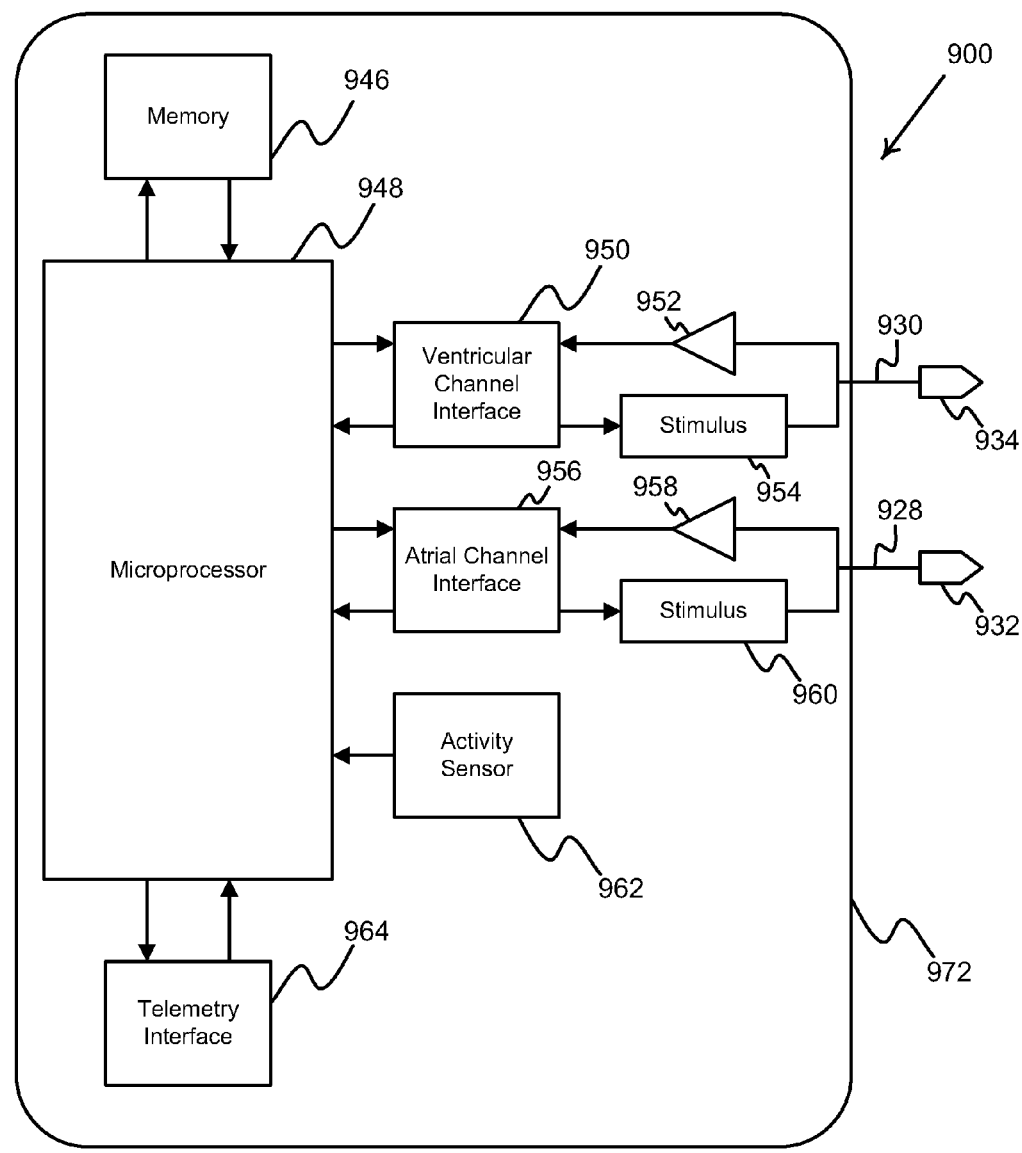
FIG. 9 is a schematic view of components of an implantable medical system in accordance with an embodiment of the invention.

Referring now to FIG. 9, some components of an exemplary implantable system 900 are schematically illustrated. The implantable medical system 900 can include an implantable medical device 972 coupled to one or more stimulation leads 930 and 928. The implantable device 972 can also include other sensors, such as activity sensor 962.

The implantable device can include a microprocessor 948 (or processor) that communicates with a memory 946 via a bidirectional data bus. The memory 946 typically comprises ROM or RAM for program storage and RAM for data storage. The implantable device can be configured to execute various operations such as processing of signals and execution of methods as described herein. A telemetry interface 964 is also provided for communicating with an external unit, such as a programmer device or a patient management system.

The implantable device can include ventricular sensing and pacing channels comprising sensing amplifier 952, output circuit 954, and a ventricular channel interface 950 which communicates bidirectionally with a port of microprocessor 948. The ventricular sensing and pacing channel can be in communication with stimulation lead 930 and electrode 934. The implantable device can include atrial sensing and pacing channels comprising sensing amplifier 958, output circuit 960, and an atrial channel interface 956 which communicates bidirectionally with a port of microprocessor 948. The atrial sensing and pacing channel can be in communication with stimulation lead 928 and electrode 932. For each channel, the same lead and electrode can be used for both sensing and pacing. The channel interfaces 950 and 956 can include analog-to-digital converters for digitizing sensing signal inputs from the sensing amplifiers and registers, which can be written to by the microprocessor in order to output pacing pulses, change the pacing pulse amplitude, and adjust the gain and threshold values for the sensing amplifiers.

It should be noted that, as used in this specification and the appended claims, the singular forms "a," "an," "and" "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A cardiac rhythm management (CRM) system for collecting patient event information, comprising:
   an implantable CRM device;
   an external interface device remote from the CRM device and comprising:
      i. a communication module adapted to be communicatively coupled to the CRM device and to request information from and receive information from the CRM device during transmission sessions,
      ii. a display device adapted to prompt a user of the CRM system to select a reason for a particular transmission session;
      iii. a user input device adapted to accept input indicating a selected reason;
      iv. a filter configured to determine whether the user of the CRM system has been prompted to enter a reason for any transmission session within a previous timeframe before prompting the user;
   wherein the external interface device is configured to store a timestamp for the transmission session and wherein the communication module is configured to transmit the selected reason and the timestamp for the transmission session to the CRM device; and
   wherein the CRM system is adapted to store the selected reason and the timestamp for the transmission session.

2. The system of claim 1 wherein the implantable CRM device further comprises a memory unit, and wherein the CRM system is adapted to store the selected reason and the timestamp information in the CRM device memory unit.

3. The system of claim 1 wherein the external interface device further comprises a memory unit, and wherein the CRM system is adapted to store the selected reason and the timestamp in the memory unit of the external interface device.

4. The system of claim 1, wherein the CRM system further comprises:
   a patient management computer system that is communicatively coupled to the external interface device, wherein the CRM system is adapted to transmit the selected reason and timestamp information to the computer system.

5. The system of claim 1 wherein the external interface device is adapted to prompt the user to choose the reason for the transmission session from a list of reasons.

6. The system of claim 5 wherein the list of reasons includes at least two of the following reasons: hospitalization, shock received, having leads checked, device reprogramming, routine follow-up, and resolving an alert.

7. The system of claim 5 wherein the communication module of the external interface device is adapted to receive recent activity information about recent activity of the CRM device and is adapted to pre-select an anticipated reason for the transmission session from the list of reasons, wherein the pre-selection of the anticipated reason is based on recent activity information from the CRM device.

8. The system of claim 1 wherein the previous timeframe is chosen based on the selected reason from a most recent past transmission session.

9. A system for collecting patient event information, comprising:
   an implantable medical device (IMD);
   an external interface device remote from the IMD and comprising:
      i. a communication module adapted to be communicatively coupled to the IMD and to request information from and receive information from the IMD during transmission sessions,
      ii. a display device adapted to prompt a user of the system to select a reason for a particular transmission session;
      iii. a user input device adapted to accept input indicating a selected reason;
      iv. a filter configured to determine whether the user has been prompted to enter a reason for any transmission session within a previous timeframe before prompting the user;
   wherein the external interface device is configured to store a timestamp for the transmission session and wherein the communication module is configured to transmit the selected reason and timestamp for the transmission session to the IMD; and
   wherein the system is adapted to store the selected reason and the timestamp for the transmission session.

10. The system of claim 9 wherein the IMD further comprises a memory unit, and wherein the system is adapted to store the selected reason and the timestamp information in the IMD memory unit.

11. The system of claim 9 wherein the external interface device further comprises a memory unit, and wherein the system is adapted to store the selected reason and the timestamp in the memory unit of the external interface device.

12. The system of claim 9, wherein the system further comprises:
   a patient management computer that is communicatively coupled to the external interface device, wherein the system is adapted to transmit the selected reason and timestamp information to the patient management computer.

13. The system of claim 9 wherein the external interface device is adapted to prompt the user to choose the reason for the transmission session from a list of reasons.

14. The method of claim 13 wherein the list of reasons includes at least two of the following reasons: hospitalization, shock received, having leads checked, device reprogramming, routine follow-up, and resolving an alert.

15. The system of claim 13 wherein the communication module of the external interface device is adapted to receive recent activity information about recent activity of the IMD and is adapted to pre-select an anticipated reason for the transmission session from the list of reasons, wherein the pre-selection of the anticipated reason is based on recent activity information from the IMD.

16. The system of claim 1 wherein the previous timeframe is chosen based on the selected reason from a most recent past transmission session.

17. A system for collecting patient event information, comprising:
   an implantable medical device (IMD);
   an external interface device remote from the IMD and comprising:
      a communication module adapted to be communicatively coupled to the IMD and to request information from and receive information from the IMD during transmission sessions,
      a display device adapted to prompt a user of the system to select a reason for a particular transmission session;
      a user input device adapted to accept input indicating a selected reason; and
      a memory unit, wherein the external interface device is configured to store a timestamp for the transmission sessions; and
      a filter configured to determine whether the user has been prompted to enter a reason for any transmission session within a previous timeframe before prompting the user; and
   a patient management computer that is communicatively coupled to the external interface device, wherein the system is adapted to transmit the selected reason and timestamp to the patient management computer;
   wherein the system is adapted to store the selected reason and timestamp in the memory unit of the external interface device;
   wherein the communication module is configured to transmit the selected reason and timestamp for the transmission session to the IMD, and
   wherein the system is adapted to store the selected reason and the timestamp in a memory unit of the IMD.

* * * * *